(12) United States Patent
Czygan et al.

(10) Patent No.: US 6,708,063 B2
(45) Date of Patent: Mar. 16, 2004

(54) CARDIAC PACEMAKER WITH POSITION DETECTOR

(75) Inventors: Gerald Czygan, Berlin (DE); Martin Lang, Grossenseebach (DE)

(73) Assignee: Biotronik Mess- und Therapiegeraete GmbH & Co. Ingernieurbuero, Berlin (DE)

( * ) Notice: Subject to any disclaimer, the term of this patent is extended or adjusted under 35 U.S.C. 154(b) by 116 days.

(21) Appl. No.: 09/740,261

(22) Filed: Dec. 18, 2000

(65) Prior Publication Data

US 2001/0012954 A1 Aug. 9, 2001

(30) Foreign Application Priority Data

Dec. 17, 1999  (DE) .......................................... 199 63 245

(51) Int. Cl.[7] .............................................. A61N 1/365
(52) U.S. Cl. .......................................... 607/19; 607/18
(58) Field of Search .................................. 607/17–19, 6, 607/7, 9

(56) References Cited

U.S. PATENT DOCUMENTS

| 4,719,921 A | * | 1/1988 | Chirife ........................ 600/516 |
| 4,860,751 A | * | 8/1989 | Callaghan ..................... 607/16 |
| 5,649,968 A | * | 7/1997 | Alt et al. ...................... 607/19 |
| 6,430,440 B1 | * | 8/2002 | McNeil et al. ................. 607/19 |
| 6,463,325 B1 | * | 10/2002 | Bolz ............................ 607/18 |

* cited by examiner

Primary Examiner—George R. Evanisko
(74) Attorney, Agent, or Firm—Hahn Loeser + Parks LLP; Stephen L. Grant

(57) ABSTRACT

An implantable cardiac pacemaker (1) comprising a control device (2) including a position detector connected to a movement sensor, wherein the position detector has a classification device (23) for recognizing short movements. Preferably the position detector has a memory device (25).

10 Claims, 5 Drawing Sheets

```
Constants:
MaxMotCnt = 525;
OrthoThres = 8;
MaxOrthCnt = 90;
```
⎱ 71

```
Initialization on application startup:
MotCnt = MaxMotCnt;
OrthoCnt = 0;
MFlag = 0;
OrthoFlag = 0;
ThresRate = (BSR+MSR)/2;
```
⎱ 72

```
Algorithm:
if (MFlag := 0) (
  if (MotCnt < MaxMotCnt)
    MotCnt += 1;
  if (MotCnt < OrthoThres)
    OrthoCnt = MaxOrthoCnt;
  else
    OrthCnt = 0;
  OrthoFlag = 0;
)
else(
  if (MotCnt != 0)
    MotCnt -= 1;
  if (OrthoCnt != 0) (
    OrthoCnt -= 1;
    OrhtoFlag = 1;
  )
  else
    OrthoFlag = 0;
);

...
if (OrthoFlag != 0 )
  if (HRF > ThresRate)
    HRF = (HRF ThresRate)/8 + ThresRate;

...
if (HRF > MSR) (
  if (OrthoFlag == 0 ) (
    Fac -= 1;
    ...
  );
);

...
// AVREF routine
if (OrthoFlag == 0)
  CETA = mREF;
else
  if (mREF > 1)
    CETA = mREF >> 1;
```
⎱ 73

Fig. 2

CARDIAC PACEMAKER WITH POSITION DETECTOR

BACKGROUND OF THE ART

It is known that changes in position on the part of patients with cardiac pacemakers frequently give rise to inappropriate or disproportionate reactions from the pacemaker. One reason for this is that the change in position gives rise to considerable variations in parameters in the circulation of the blood, more particularly because of the altered influence of the force of gravity. Frequently, a variation in intercardial or transthoracal impedance, caused by a change in position, is misinterpreted by a control system of the pacemaker as physical activity, to which the pacemaker reacts with a change in the heart rate which is inappropriate in relation to the change in position. That gives rise to problems. Admittedly, an inappropriate variation in heart rate of that kind is generally not life-threatening, but it is perceptible for the patient. In particular a patient who is lying down and who merely changes his position from lying on the right side to the left side will experience changes in heart rate which are caused thereby as being uncomfortable. A more serious consideration is that, in the case of self-adapting pacemakers, such unnecessary changes in heart rate can have an adverse influence on the adaptation performance of the pacemaker, with the result that the pacemaker then no longer adequately reacts to physical loads and stresses.

In order to avoid that, pacemakers are provided with detectors for detecting changes in position. U.S. Pat. No. 5,593,431, to Sheldon, discloses a pacemaker with an implanted accelerometer as a position detector. The accelerometer which acts in three axes measures the direction of the pull of gravity and determines therefrom the position of the patient. As however implants generally have a tendency to turn within the body of the patient, there is the risk of the reference system of the accelerometer suffering from displacement. That makes gravitational measurement unreliable and position detection uncertain. It is also known for signals of an accelerometer to be subjected to frequency analysis in order to determine therefrom rest and activity phases, as disclosed in Thompson, U.S. Pat. No. 5,233,984. A disadvantage with that method is that a change between a rest phase and an activity phase does not necessarily correlate with a change in position. That gives rise to detection errors, resulting in an only low level of accuracy in terms of position sensing.

The object of the present invention is to provide a pacemaker which has a reliable detection device for changes in position, which enjoys long-term stability.

SUMMARY OF THE INVENTION

In accordance with the invention that object is attained by a pacemaker having the features of claim 1. Advantageous developments are set forth in the appendant claims.

In accordance with the invention, in an implantable cardiac pacemaker comprising a control device including a position detector connected to a movement sensor, it is provided that the position detector has a classification device for the recognition of short movements. The invention is based on the notion that a short signal from the movement sensor is a standard or benchmark for a change in position. It accordingly turns away from the approach followed in the state of the art, namely, ascertaining changes in position by interpretation of contents of the signals from the movement sensor. This is based on the realization that it is crucially important to ascertain the change between different positions of the body, and that it is possible to forego determining the absolute position of the body of the patient. The invention realized that classification in accordance with the duration of the signal from the movement sensor can be used not only for reliably detecting changes in position but in addition also advantageously for determining the hemodynamic relevance of the change in position. This is based on the realization that a change in position is all the more significant in terms of the hemodynamics of the circulation of the blood, the more rapidly the change in position takes place; conversely, a change in position which takes place slowly is only of slight hemodynamic relevance.

The pacemaker according to the invention also has the advantage that it is not really expensive. The movement sensor can be a simple known activity sensor, an expensive multi-axis accelerometer is not required; linearity and sensitivity are only of subordinate significance. As the movement sensor of the pacemaker according to the invention, in contrast to the three-axis accelerometer, does not require a given reference system, the pacemaker according to the invention is robust in relation to the implant turning, thereby improving long-term reliability.

In order to be able to determine the duration of a signal from the movement sensor the classification device desirably has a short-term counter and a switch device. The term counter in accordance with the present invention is to be interpreted broadly; it includes both event counters and also time counters. Admittedly, counters are usually adapted to operate in a discrete manner, but counters which operate continuously should not be excluded. An event counter which is adapted to count clocks while a movement signal is applied is particularly advantageous. As a clock signal is usually already present in pacemakers for a microprocessor, the additional expenditure required for the counter is thus slight.

Desirably the comparison device is such that at the end of the movement signal it compares a counter state to a predeterminable threshold value and outputs a position change signal. The predeterminable threshold value makes it possible to achieve a patient-specific setting for the time duration, up to which a signal from the movement sensor is to be detected as a change in position. In that way the pacemaker according to the invention can be matched to the hemodynamics of the respective patient. The switch device is possibly also connected to a telemetry device of the pacemaker; that makes it possible to modify the threshold value from the exterior even after implantation. At its output the switch device provides a position change signal which can assume various states and which is an input signal for other function modules of the control device.

Advantageously the position detector has a memory device. The memory device stores past movements, in which respect the memory device has only a limited depth of recollection. The memory device represents an indicator as to whether prior to a movement to be classified other movements have already taken place, that is to say whether an activity state is involved, or whether previously there was a rest phase, that is to say a passivity state is involved. As a change in position from a passivity state is hemodynamically more relevant than one from an activity state, the memory device is advantageous in terms of evaluating the hemodynamic relevance of a change in position. The position detector is therefore not limited to signals which are supplied at the present time by the sensor, but it can additionally be adapted to evaluate signals in terms of preceding movements; that permits more accurate recognition of changes in position. The memory device is connected to the switch device; the switch device is designed in such a way that, in a corresponding manner as in the case of the short-term counter, at the end of a movement signal, it compares the value of the memory device to a predeterminable second threshold value. The predeterminable second threshold value makes it possible to achieve a patient-specific setting for the memory device. Desirably, the switch device is designed for interlinking the comparison results of the short-term counter and the memory device, in such a way that, for the output of a position change signal, the movement signal must be correspondingly shorter, the higher the activity state. The cardiac pacemaker then involves a physiologically correct behavior, whereby a change in position correspondingly more requires an appropriate reaction on the part of the pacemaker, the correspondingly less activity or even no activity at all has preceded, and vice-versa.

Desirably, the memory device has an integrator. The integrator is adapted to add periods of time, during which a signal of the movement sensor is applied and for subtracting periods of time during which no signal from the movement sensor is applied. It thus acts as a memory for preceding movements. An adjustable maximum in respect of the value of the integrator limits the depth of recollection.

In a preferred embodiment, the short-term counter and the integrator are integrated into a counter. Besides a reduced level of expenditure, that affords the advantage that only one threshold value needs to be set and nonetheless the physiologically correct interaction between preceding activity and duration of the movement signal is retained.

Desirably, there is provided an elapsed time counter, at the input of which the position change signal is applied and at the output of which a blocking signal is outputted. Such a counter provides an information signal, as to how long the position change signal is already applied, and thus makes it possible to determine the time which has passed since the detected change in position. That makes it possible for the control device to react in time-matched relationship to a change in position, for example to limit its reaction to a given period of time.

Desirably there is provided a cancellation or clearing device for the blocking signal, the triggering device thereof being connected to the movement sensor. The cancellation or clearing device provides that, upon the occurrence of a fresh movement, the position change signal is canceled or cleared, and the pacemaker can react to the fresh movement, without being adversely affected by the position change signal.

Preferably, the control device has a position-dependent heart rate limiter. That can provide that the stimulation frequency does not rise above a given limit value, in the event of movements of the patient which are due to changes in position. Desirably, a position change signal and a heart rate signal are applied to the heart rate limiter. The heart rate signal is a signal calculated by the control device, for exciting the cardiac muscle. In dependence on the position change signal, the heart rate limiter limits the calculated heart rate signal by means of an adjustable limiting function and outputs it. The term limiting function is used to mean a function whose output value rises less than its input value. The heart rate limiter can be such that, at a value in respect of the calculated heart rate signal which is higher than a limit value, the outputted heart rate signal is of precisely that limit value; that is referred to as rigid limitation. Advantageously however the heart rate limiter is adapted to afford a flexible limitation effect, such that, at a value of the calculated heart rates, which is higher than a limit value, the value of the outputted heart rate is between the calculated heart rate and the limit value.

The control device advantageously has an inhibitor. The inhibitor serves to prevent adaptation of parameters of the control device, induced by a change in position. That ensures that the parameters are not altered by changes in position in such a way that the frequency-adaptive behavior of the pacemaker is worsened. For that purpose, it is desirably provided that the inhibitor is cooperatively connected to an adaptation module in such a way that adaptation is blocked in position-dependent manner. That avoids self-adapting parameters of the pacemaker being influenced during the application of the position change signal, as otherwise the behavior of the pacemaker could be worsened in a situation involving a physical load.

In an alternative embodiment the implantable pacemaker is connected to a sensor for the physiological demand, in particular an impedance sensor for measuring intercardial or transthoracal impedance. In addition, this pacemaker has control means for setting a stimulation rate or heart rate in dependence on a signal coming from the physiological demand sensor. In that case, control of the heart rate can be limited in such a way that the changes in rate as a result of the physiological demand are limited in respect of their magnitude in particular upwardly but also downwardly. That therefore affords a band of permitted heart rates. In the alternative pacemaker the position of that band, that is to say the position of the upper and lower rate limits, is determined by a signal from the movement sensor. In that way it is possible to achieve a rate limitation effect in the case of a change in position, just as an increased stimulation rate can be permitted in the event of continuous movement and increased metabolic demand.

BRIEF DESCRIPTION OF THE DRAWINGS

The invention is described in greater detail hereinafter with reference to the accompanying drawing showing preferred embodiments of the invention. In the drawing:

FIG. 2 shows a high-level language listing for the storage operation in a second embodiment of the invention.

DETAILED DESCRIPTION OF THE INVENTION

Figure 1:
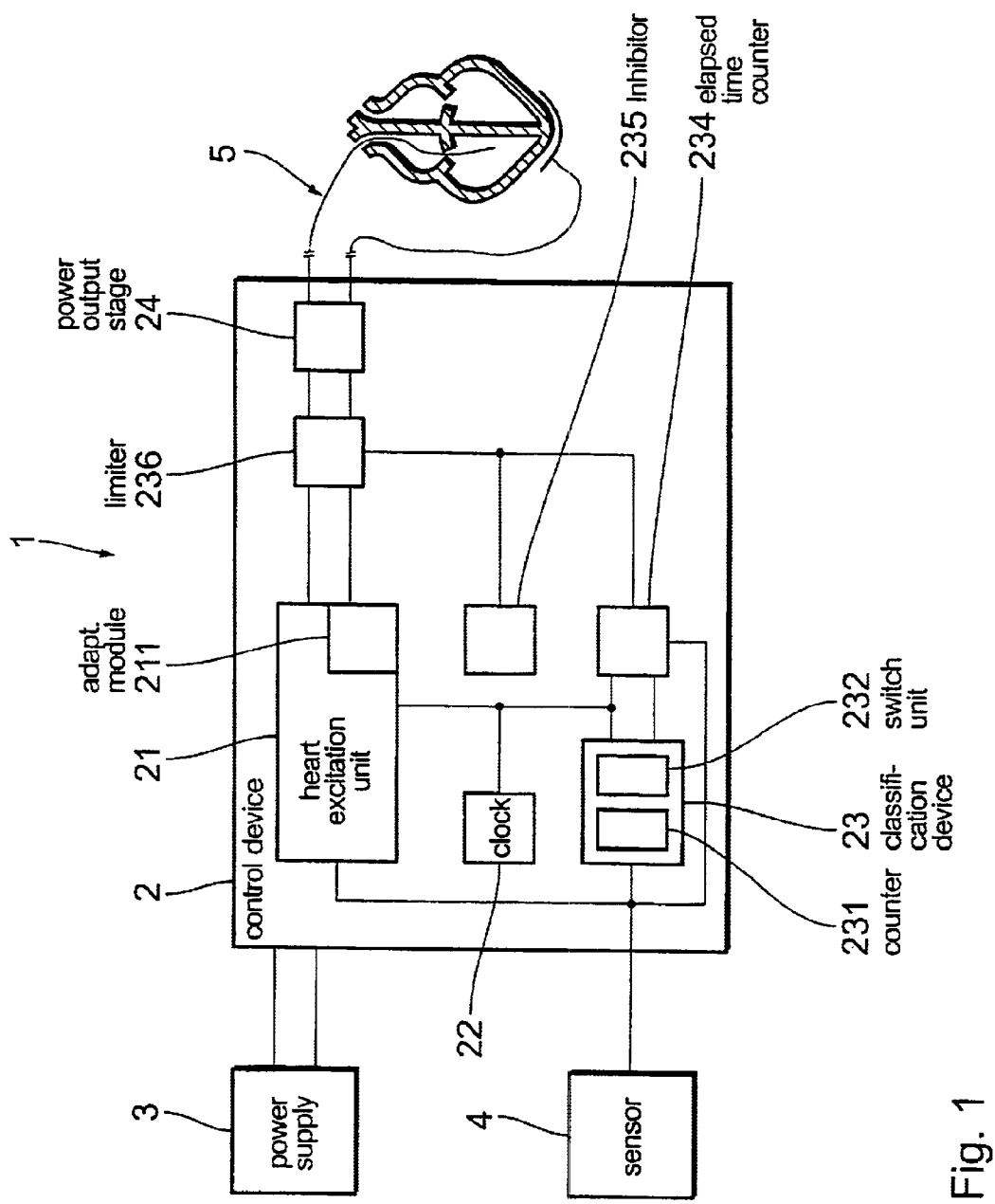
FIG. 1 is a diagrammatic view of a pacemaker according to the invention with a movement sensor and a control device having a position detector.
Figure 3A:
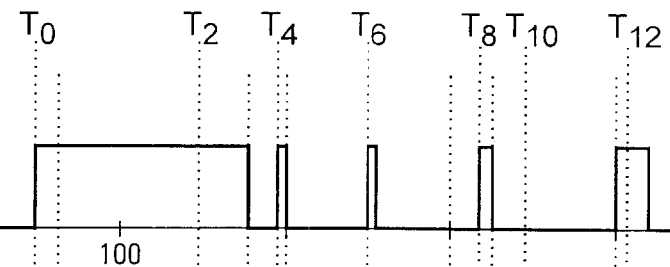
FIGS. 3a–3d shows graph representations of some signals in an embodiment of the invention.
Figure 3B:
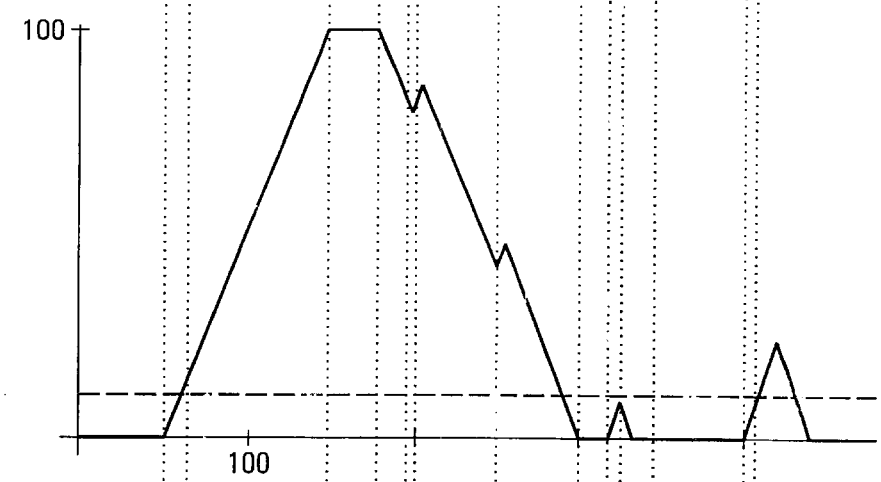
Figure 3C:
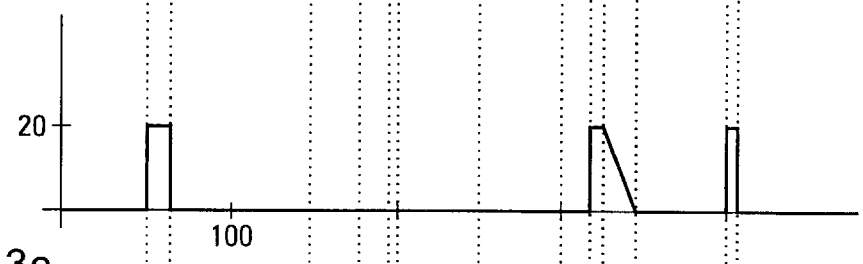
Figure 3D:
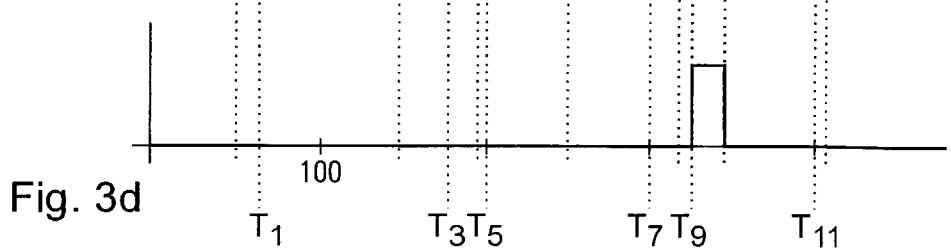
Figure 4A:
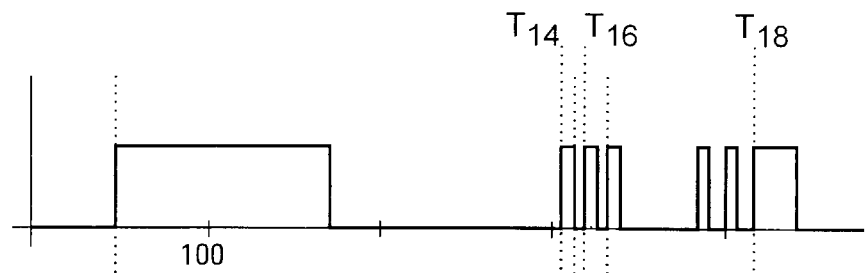
FIGS. 4a–4d shows further graph representations of some signals.
Figure 4B:
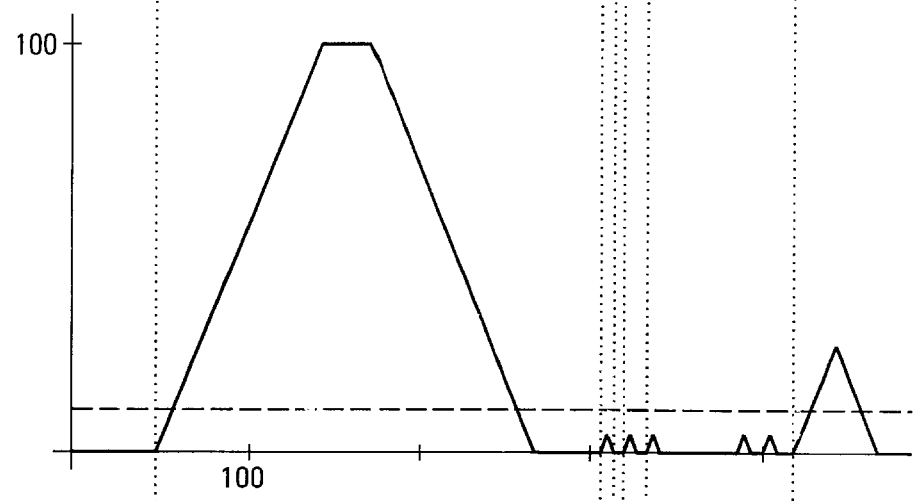
Figure 4C:
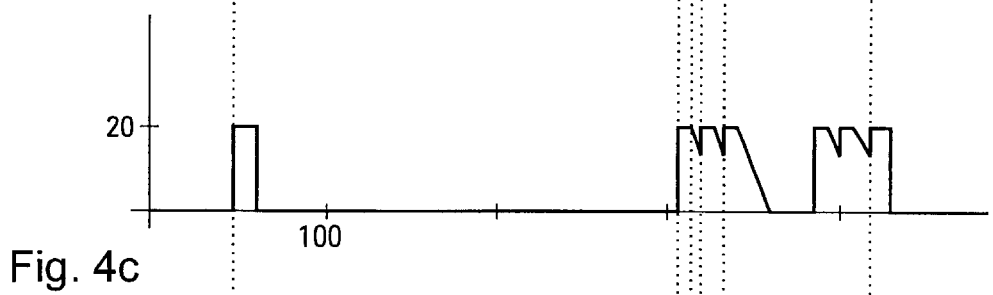
Figure 4D:
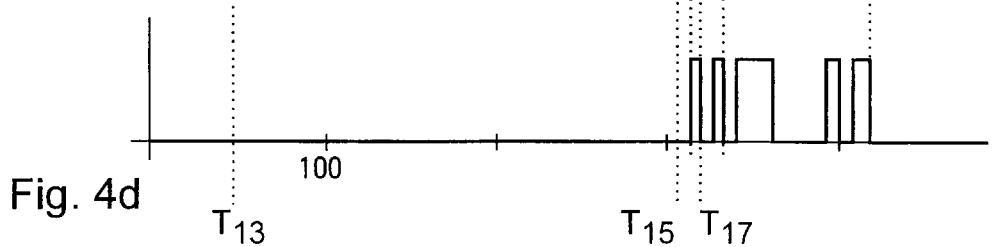

FIG. 1 shows a cardiac pacemaker in accordance with an embodiment of the invention. The pacemaker 1 includes in a housing (not shown) a control device 2 connected to a power supply 3 and a movement sensor 4. The drawing also symbolically represents an electrode set 5 which is intended to be arranged at a heart and which is connected to the pacemaker 1.

The movement sensor 4 is in the form of a simple activity sensor, as is known from the state of the art to a man skilled in the art. Examples of such activity sensors are acceleration pickups and vibration pickups. As the movement sensor 4 is only intended to determine the presence or absence of a movement, it can be of a comparatively simple and robust structure. As it is sufficient to provide for determining the presence or absence of a movement, independently of direction, accurate positioning of the movement sensor 4 in the implanted state, and whether that position is also maintained with long-term stability, are not crucially important considerations. Preferably the movement sensor is arranged integrated into the housing of the pacemaker 1.

As its core the control device 2 has a heart excitation unit 21, and is connected to the power supply 3 and by way of a power output stage 24 to the electrode set 5. The heart excitation unit 21 is adapted to calculate from signals from the movement sensor 4 and/or other sensors (not shown), a heart rate which is outputted in the form of a pulse series to the electrode set 5. It includes an adaptation module 211 which is designed for automatic adaptation of parameters which are used in calculating the heart rate. Such a heart excitation unit 21 with adaptation module 211 is known from the state of the art to the man skilled in the art and is therefore not described in greater detail hereinafter.

The control device 2 also has a clock 22, a classification device 23, an elapsed time counter 234, an inhibitor 235 and a limiter 236. These are connected as necessary by means of connections (not shown) to the power supply 3.

The clock 22 is in the form of a cycle generator which outputs a clock pulse for each heartbeat. That means that the clock pulses are not outputted at a constant frequency, but the frequency of the clock pulses depends on the current heart rate. However, the possibility of providing a conventional timer unit as the clock should not be excluded. The clock provides the time base for the pacemaker 1. Besides being connected to the heart excitation unit 21, its output is also connected to the classification device 23 and the elapsed time counter 234.

The classification device 23 includes a counter 231 and a switch unit 232. The counter 231 is in the form of a maximum-limited up/down counter with a counting input and a control input, as well as a counter state output. The clock 22 is connected to its counting input while the movement sensor 4 is connected to its control input which determines the counting direction. The counter 231 also has a settable maximum whose value cannot be exceeded by the counter state; in addition, it cannot fall below the value zero. When a signal from the movement sensor 4 is applied to the control input of the counter 231 the counter 231 is switched as an up-counter; the clock signals from the clock, which are applied to the counting input, are added to the counter state. When no signal from the movement sensor 4 is applied to the control input the counter 231 is switched as a down-counter; the clock signal from the clock 22, which is applied to the counting input, reduce the counter state.

The output of the counter 231 is applied to an input of the switch unit 232. The switch unit 232 is such that, at the end of a movement, that is to say as long as the signal from the movement sensor 4 is absent, the switch unit 232 compares the counter state of the counter 231 to an adjustable threshold value and outputs a position change signal when the counter state is less than the threshold value. In order to recognize when the signal of the movement sensor 4 ends, there is provided a further input of the switch unit 232, to which the movement sensor 4 is applied; the absence of the signal from the movement sensor 4 triggers off in the switch unit 232 the step of comparison between the counter state and the threshold value. Alternatively, it can also be provided that the beginning of a reduction in the counter state is taken as the end of the signal of the movement sensor 4; admittedly, that involves a delay by a clock pulse with respect to the true end of the signal from the movement sensor, but this saves the expense of an additional input.

The position change signal is applied to an input of the elapsed time counter 234 and provides that the elapsed time counter 234 is set to a presettable delay value and, starting therefrom, counts downwards to zero. During the elapse time the elapsed time counter 234 outputs a blocking signal. An output of the elapsed time counter 234 is connected to the inhibitor 235 and the limiter 236. The blocking signal is applied thereto. The elapsed time counter also has a cancellation or clearing input to which the movement sensor 4 is applied. If a signal from the movement sensor 4 occurs during the operation of the elapsed time counter 234, the elapsed time counter 234 is cleared and the output of the blocking signal is terminated.

The inhibitor 235 has an input to which the blocking signal is applied, and an output which is connected to the adaptation module 211 of the heart excitation unit 21. The inhibitor 235 is in an active state as long as the blocking signal is applied to its input; otherwise it is in a passive state. It cooperates with the adaptation module 211 in such a way that in its active state it blocks the adaptation module 211. The fact that parameter adaptation is blocked ensures in particular that the changes in position do not result in an unwanted variation in a response factor parameter.

The limiter 236 is arranged between the heart excitation device 21 and the power output stage 24. For that purpose it is connected by a signal input to the output of the heart excitation device 21 and by a signal output to the input of the power output stage 24. It also has a control input to which the blocking signal is applied. The limiter 236 is in an active state as long as the blocking signal is applied to its control input; otherwise it is in a passive state. In its active state it limits the frequency of the heart rate applied to the signal input, if it is greater than an adjustable threshold frequency ("ThresholdRate"). In the case of the limiter 236 illustrated in the specific embodiment, limitation in terms of the heart rate is effected "flexibly" or "softly", in other words, the frequency of the heart rate (HRout) outputted at the power stage 24 is a smaller amount above the threshold frequency than the frequency of the heart rate applied by the heart excitation device 21 (HRin). To put that more precisely, the outputted heart rate in the limitation situation is determined by the following formula:

$$HRout=(HRin-ThresholdRate)/8+ThresholdRate.$$

That means that even in the limitation situation, that is to say when the blocking signal is applied to the limiter 236 and the applied heart rate is above the threshold value, the behavior of the pacemaker 1 is still physiologically correct, more specifically it is at least slightly positively chronotropic. In addition the limiter 236 is such that the outputted frequency is limited to an absolute maximum value ("MCLR"). The limiter 236 is of a reaction-free nature so that, even if the outputted heart rate were to be above the absolute maximum value, a reduction in the response factor is prevented. That avoids parameters of the pacemaker being adversely influenced, even in the event of extreme changes in position, which result in a vigorous reaction on the part of the pacemaker 1.

The above-mentioned constituent parts of the control device 2 do not necessarily need to be in the form of independent components in hardware form; they may also be in the form of modules of the control device 2, in which case then the control device has a microcontroller and a memory in which a program code is stored. An embodiment of such a program code which is stored in the memory is shown in FIG. 2.

Constants are defined in a first section 71. These involve the maximum limit ("MaxMotCnt") of the counter, the threshold value ("OrthoThres") of the switch unit and the delay value ("MaxOrthCnt") of the elapsed time counter.

Variables and indicators are initialized in a second section 72. The value of the counter ("MotCnt") is set to the maximum limit, the elapsed time counter ("OrthoCnt") is set to zero, indicators for movement ("MFlag") and changes in position ("OrthoFlag") are set to zero and the threshold frequency ("ThresRate") is determined.

The modules of the control device are defined in a third section 73. For that purpose, a first step involves checking whether a movement signal is applied. If that is the case the value of the counter is increased by one insofar as the maximum limit has not yet been reached; as a precaution, if the value of the counter is less than the threshold value, the elapsed time counter is set to the delay value, but otherwise to zero; in addition the position change indicator is set to zero. If however the situation which obtains is that a movement sensor is not applied, then the value of the counter is reduced by one if it has not yet reached zero; in addition, if the elapsed time counter is of a value which is different from zero, the value of the elapsed time counter is reduced by one and the indicator for changes in position is set, but otherwise only the indicator for changes in position is cleared. In a subsequent second step a check is made to ascertain whether the heart rate outputted by the heart excitation device 21 is greater than the threshold frequency. If that is the case a reduced heart rate is calculated by a procedure whereby a difference is formed between the heart rate and the threshold frequency, divided by eight and added to the threshold frequency.

The mode of operation of the pacemaker according to the invention in the position detection procedure will be described hereinafter by means of two examples illustrated in FIGS. 3 and 4.

In FIG. 3 a signal configuration for the movement sensor 4 is illustrated a). It will be seen that there are a relatively long movement phase at the beginning and a plurality of shorter subsequent movement phases. FIG. 3 b) show in association in respect of time the counter state of the counter 231; the threshold value is also illustrated by means of a broken horizontal line. The value of the elapsed time counter 234 is shown at c). The position change signal is shown at d). Pulses of the clock are represented on the abscissa.

It will be seen that, at the beginning of the first movement phase at a time $T_0$ the counter 231 counts up, starting from zero; at the same time as a precaution the elapsed time counter 234 is loaded with the delay value. A position change signal is not outputted. In the further course of the first movement phase the counter state b) of the counter is increased and at time $T_1$ exceeds the threshold value represented by the broken horizontal line. At that time $T_1$ the movement phase has attained a duration which is too long for it to involve a change in position; no position change signal is outputted at the conclusion of that movement phase. Therefore the classification device according to the invention clears the elapsed time counter 234 which was already loaded as a precaution, by setting it to zero. At a time $T_2$ the counter 231 reaches its maximum and the counter state 231 remains at that value for the remaining duration of the first movement phase. With the end of the first movement phase at time $T_3$ the counter state a) of the counter 231 begins to decrease. A position change signal is not outputted. At the time $T_4$ a second a movement phase begins, which is shorter than the first one. The counter 231 counts up and the counter state a) is increased until the second movement phase terminates at a time $T_5$. Although the second movement phase is sufficiently short to be able to be a change in position, the classification device does not output a position change signal as the counter state a) of the counter 231 is greater than the threshold value (horizontal line). In that case the counter 231 acts as a memory in respect of the classification device as so-to-speak it still knows that shortly before that a movement had taken place and thus there is no need for a particular reaction to a possible change in position. At a time $T_6$ a third movement phase begins, which corresponds to the second movement phase. After that movement phase the counter 231 counts down again until its counter state a) reaches the value zero at a time $T_7$. A fourth movement phase begins at a time $T_8$. The counter 231 counts up, the counter state a) is increased and the elapsed time counter 234 is as a precaution loaded with the delay value c). The fourth movement phase terminates at a time $T_9$, the counter state a) being below the threshold value (horizontal line). The classification device therefore starts the elapsed time counter 234. It counts down and, in so doing, the position change signal d) is outputted until at a time $T_{10}$ the elapsed time counter 234 reaches the value zero and output of the position change signal d) ends. A fifth movement phase begins at a time $T_{11}$. The counter 231 counts up and the elapsed time counter 234 is loaded as a precaution with the delay value. At a time $T_{12}$ the counter state b) exceeds the threshold value, that is to say the movement phase is too long to be a change in position. The elapsed time counter 234 is therefore set to zero and no position change signal is outputted at the end of the fifth movement phase.

FIG. 4 shows a further functional example for the pacemaker according to the invention. As in the case of FIG. 3, a signal configuration of the movement sensor 4 is illustrated a), the counter states of the counter 231 are shown at b), values of the elapsed time counter 234 are illustrated at c) and a position change signal is shown at d). Pulses of the clock are shown on the abscissa. The sixth movement phase beginning at a time $T_{13}$ substantially corresponds to the first and is not described in greater detail hereinafter. A seventh movement phase which includes a plurality of individual movements begins at a time $T_{14}$. At the beginning of the movement phase at time $T_{14}$ the counter state b) of the counter 231 is increased, and as a precaution the elapsed time counter 234 is set to the delay value c). At the end of the first individual movement at a time $T_{15}$ the counter state a) is below the threshold value (broken horizontal line) and the classification device starts the elapsed time counter 234 and outputs the position change signal d). With the beginning of the second individual movement at a time $T_{16}$ the counter state b) of the counter 231 is again increased, the elapsed time counter is set as a precaution to the delay value c) and the position change signal d) is cleared. The latter ensures that the pacemaker can suitably react to the current movement without possibly being adversely affected by the position change signal. If the following individual movement which begins at a time $T_{17}$ is a short movement (as shown), then at the end of that individual movement at a time $T_{18}$ the counter state a) is below the threshold value; thereupon the elapsed time counter 234 is started and the position change signal d) is outputted. If however a subsequent movement is a movement of longer duration (like that beginning at a time $T_{19}$), then the counter state b) increases beyond the threshold value and no further position change signal d) is outputted.

Figure 5:
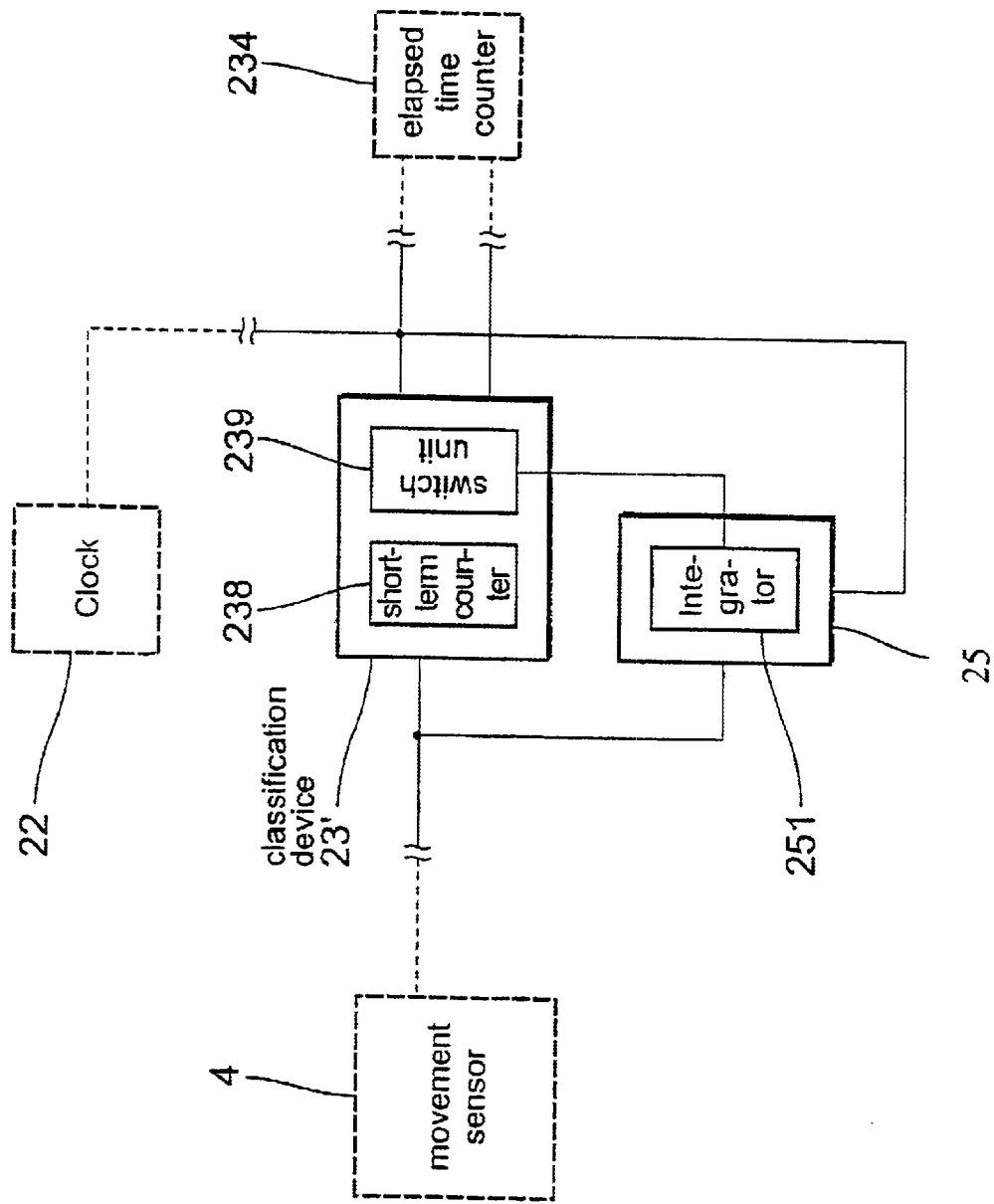
FIG. 5 shows a pacemaker according to the invention in accordance with a second embodiment thereof.

FIG. 5 shows a fifth embodiment of a pacemaker according to the invention. It has in the form of an integrator 251 an independent memory device 25 while the memory device 25 in the first embodiment shown in FIG. 1 is integrated into the counter 231. The classification device 23' includes a short-term counter 238 and a switch unit 239.

The integrator 251 is in the form of a dissipative integrating device, in other words, it increases its value when a signal from the movement sensor 4 is applied, and it decreases its value when no signal from the movement sensor 4 is applied.

For that purpose it is in the form of a maximum-limited up/down counter having a counting input and a control input and a sum value output. The integrator 251 however does not necessarily need to be in the form of a counter, but it may also involve another component with an integrating function, preferably a low pass-like element such as for example an RC-element. The clock 22 is connected to a counting input of the integrator 251, while the movement sensor 4 is connected to its control input which determines the counting direction. The integrator 251 also has an adjustable maximum, the value of which cannot be exceeded by the counter state; in addition, it cannot drop below the value zero. While the signal from the movement sensor 4 is applied the integrator 251 sums the clock pulses from the clock 22. While no signal from the movement sensor 4 is applied the integrator 251 decreases its value by one, with each clock pulse. The value of the integrator 251 represents a measurement for the extent of the movements which were detected by the movement sensor 4 in an immediate past. In that respect, only a certain region of the more recent past is relevant, which is determined by the level of the adjustable maximum. The integrator 251 thus acts as a memory for the pacemaker, which is restricted in terms of its depth of recollection.

The short-term counter 238 is in the form of a resettable event counter. It has a counting input to which the clock 22 is applied, a switching input to which the movement sensor 4 is applied and a counter state output to which the switch unit 239 is connected. The switching input is such that it is edge-controlled. The short-term counter 238 is of such a design configuration that, upon an increase in a signal from the movement sensor 4 at the switching input, its counter state is reset to zero and that it counts the number of clock pulses from the clock 22 while a signal is applied to the switching input by the movement sensor 4.

The switch unit 239 has inputs which are connected to the integrator 251 and the short-term counter 238 respectively, and an output which is adapted to output a position change signal. The switch unit 239 is such that, at the end of a movement, that is to say with the absence of the signal from the movement sensor 4, it compares the sum value of the integrator 251, which is applied at its first input, to an adjustable threshold, and also compares the counter state of the short-term counter which is applied to its second input, to an adjustable threshold duration; it is only when both inputs are below the threshold and the threshold duration respectively, that the position change signal is outputted by way of the output of the switch unit 239. Therefore, two conditions must be cumulatively satisfied so that the position change signal can be outputted in relation to a movement: the movement to be evaluated must have been sufficiently short, more specifically shorter than the threshold duration; and not too many movements may have taken place in the more recent past, more specifically fewer than are determined by the threshold of the integrator. Both conditions can be adapted independently of each other to individual factors of a patient, by varying the threshold and the threshold duration respectively.

What is claimed is:

1. An implantable cardiac pacemaker for a user imposing a physiological demand thereon, the pacemaker capable of adapting to changes in physiological parameters, the pacemaker comprising:

a movement sensor that generates a movement signal in the presence of a movement of the pacemaker and no signal in the absence of pacemaker movement; and a control device comprising a classification device, connected to the movement sensor, for recognizing pacemaker movements by measuring a duration of the movement signal;

wherein the classification device comprises a memory device, a short-term counter and a switch device; and wherein the switch device compares a state of the counter at an end of the movement signal to at least one predeterminable threshold value and outputs a position change signal.

2. The implantable cardiac pacemaker of claim 1, characterized in that the memory device has an integrator.

3. The implantable cardiac pacemaker of claim 1, wherein the control device further comprises a position-dependent heart rate limiter.

4. The implantable cardiac pacemaker of claim 3, wherein the heart rate limiter receives the position change signal from the switch device and a heart rate signal calculated by the control device.

5. The implantable cardiac pacemaker of claim 4 wherein the control device further comprises an inhibitor and an adaptation module;

the adaptation module being cooperatively connected to the inhibitor so that adaptation of the control device is prevented during the presence of the position change signal.

6. The implantable cardiac pacemaker of claim 3, further comprising:

a physiological demand sensor connected to the pacemaker, the physiological demand sensor being in the form of an impedance sensor for measuring an intracardial or transthoracal impedance of the user; and a control means for setting a stimulation or heart rate in dependence on a signal from the physiological demand sensor, wherein the change in the stimulation or heart rate can be lastingly limited in such a way that the heart rate limitation is effected in dependence on the movement signal from the movement sensor.

7. The implantable cardiac pacemaker of claim 1, further comprising:

a physiological demand sensor connected to the pacemaker, the physiological demand sensor being in the form of an impedance sensor for measuring an intracardial or transthoracal impedance of the user; and a control means for setting a stimulation or heart rate in dependence on a signal from the physiological demand sensor, wherein the change in the stimulation or heart rate can be lastingly limited in such a way that the heart rate limitation is effected in dependence on the movement signal from the movement sensor.

8. The implantable cardiac pacemaker of claim 1, further comprising an elapsed time counter having an input that receives the position change signal from the switch device and an output that generates a blocking signal.

9. The implantable cardiac pacemaker of claim 8 wherein the elapsed time counter comprises a clearing device for the blocking signal, the clearing device having a triggering device connected to the movement sensor.

10. An implantable cardiac pacemaker for a user imposing a physiological demand thereon, the pacemaker capable of adapting to changes in physiological parameters, the pacemaker comprising:

a movement sensor that generates a movement signal in the presence of a movement of the pacemaker and no signal in the absence of pacemaker movement; and a control device comprising a classification device, connected to the movement sensor, for recognizing pacemaker movements by measuring a duration of the movement signal;

wherein the classification device comprises a memory device, a short-term counter and a switch device; and wherein the memory device has an integrator.

* * * * *